United States Patent [19]

Liu

[11] Patent Number: 5,931,815

[45] Date of Patent: Aug. 3, 1999

[54] MULTIFUNCTIONAL SAFETY INFUSION SET WITH INJECTION NEEDLE RETRACTABLE IN A WING-EQUIPPED SHEATH

[76] Inventor: Wen-Neng Liu, 19508 Nicholas Ave., Cerritos LA., Calif. 90701

[21] Appl. No.: 08/916,929

[22] Filed: Aug. 22, 1997

[51] Int. Cl.[6] .................................................. A61M 5/00
[52] U.S. Cl. ......................... 604/171; 604/177; 604/198
[58] Field of Search .................................... 604/174, 177, 604/171, 162, 158, 164, 167, 110, 198, 195, 197, 263, 192, 905, 283, 256, 175, 533; 128/919

[56] References Cited

U.S. PATENT DOCUMENTS

| | | | |
|---|---|---|---|
| 4,425,120 | 1/1984 | Sampson et al. | 604/198 |
| 4,676,783 | 6/1987 | Jagger et al. | 604/177 |
| 4,743,233 | 5/1988 | Schneider | 604/198 |
| 4,820,288 | 4/1989 | Isono | 604/283 |
| 4,927,417 | 5/1990 | Moncada et al. | 604/198 |
| 4,963,132 | 10/1990 | Gibson | 604/256 |
| 5,057,093 | 10/1991 | Clegg et al. | 604/283 |
| 5,088,982 | 2/1992 | Ryan | 604/198 |
| 5,108,376 | 4/1992 | Bonaldo | 604/177 |
| 5,250,040 | 10/1993 | Parks et al. | 604/283 |
| 5,259,843 | 11/1993 | Watanabe et al. | 604/256 |
| 5,382,240 | 1/1995 | Lam | 604/177 |
| 5,573,512 | 11/1996 | van den Haak | 604/198 |
| 5,674,201 | 10/1997 | Steinman | 604/177 |
| 5,674,209 | 10/1997 | Yarger | 604/256 |
| 5,800,400 | 9/1998 | Hogan | 604/177 |

*Primary Examiner*—Ronald Stright
*Attorney, Agent, or Firm*—Rosenberg, Klein & Bilker

[57] ABSTRACT

A multifunctional safety infusion set with injection needle retractable in a wing-equipped sheath. The infusion set includes a connecting tube having an upper and a lower engaging sections respectively near top end and bottom end of the connecting tube. The bottom end of the connecting tube is connected with an infusion tube, while the top end thereof is connected with an injection needle. The infusion set further includes a wing-equipped sheath slidably fitted around the connecting tube. When the sheath is slid downward to engage with the lower engaging section of the connecting tube, the injection needle protrudes outside the sheath for injection. After the injection is completed, the sheath is slid upward to engage with the upper engaging section of the connecting tube so as to totally enclose and hide the injection needle in the sheath without protruding outside. Therefore, the accidental impalement of medical personnel is avoided and the safety is ensured.

3 Claims, 10 Drawing Sheets

MULTIFUNCTIONAL SAFETY INFUSION SET WITH INJECTION NEEDLE RETRACTABLE IN A WING-EQUIPPED SHEATH

BACKGROUND OF THE INVENTION

A multifunctional safety infusion set with injection needle retractable in a wing-equipped sheath. After the injection is completed, the injection needle is totally enclosed and hidden in the sheath without protruding outside. Therefore, the accidental impalement of medical personnel is avoided.

In the existing medically used intravenous (I.V.) fustula set, scalp vein set and general dropper infusion syringe, a single injection needle is connected with an infusion hose for hypodermic injection. A needle cap is disposed on the syringe for shielding the needle on the front side. In injection, the needle cap is withdrawn. After the injection is completed, the needle is again shielded by the needle cap. The needle cap has a very small fitting hole. Therefore, when inserting the needle back into the needle cap, it often takes place that the medical personnel are accidentally impaled by the needle and infected with AIDS, hepatitis, etc.

Moreover, in the medical dropper equipments such as A.V. fustula set, scalp vein set, dropper infusion syringe and hypodermic injection needle, a wing type fixing plate is provided. However, it is impossible to replace various types and sizes of needles with each other so that each medical unit must prepare multiple types of needles for various uses. This leads to inconvenience in use.

SUMMARY OF THE INVENTION

It is a primary object of the present invention to provide a multifunctional safety infusion set with injection needle retractable in a wing-equipped sheath. The sheath is slidably fitted around a connecting tube of the infusion set. After the injection is completed, the sheath is slid upward to engage with an upper end of the connecting tube so that the injection needle is totally enclosed and hidden in the sheath before discarded. Therefore, the accidental impalement and infection of medical personnel or other people is avoided. The infusion set of the present invention has simple structure and is widely applicable to I.V. fustula set, scalp vein set, hypodermic syringe and general dropper infusion set. Therefore, the waste of medical resource is reduced.

The present invention can be best understood through the following description and accompanying drawings, wherein:

DETAILED DESCRIPTION OF THE PREFERRED EMBODIMENTS

Please refer to FIGS. 1 to 5. The infusion set of the present invention includes a connecting tube 1 having an upper and a lower engaging sections 11, 12 around the outer periphery. The bottom end of the connecting tube 1 is connected with an infusion tube 2, while the top end thereof is connected with an injection needle 3. A wing-equipped sheath 4 is slidably fitted around the connecting tube 1. The sheath 4 has a fitting hole 41. The wall of the fitting hole 41 is formed with a connecting section 411 for slidably engaging with the upper and lower engaging sections 11, 12 of the connecting tube 1. When the connecting section 411 of the sheath 4 is engaged with the upper engaging section 11, the injection needle 3 is retracted and hidden in the fitting hole 41 of the sheath 4 without protruding outside so as to avoid accidental impalement of other people.

Figure 1:
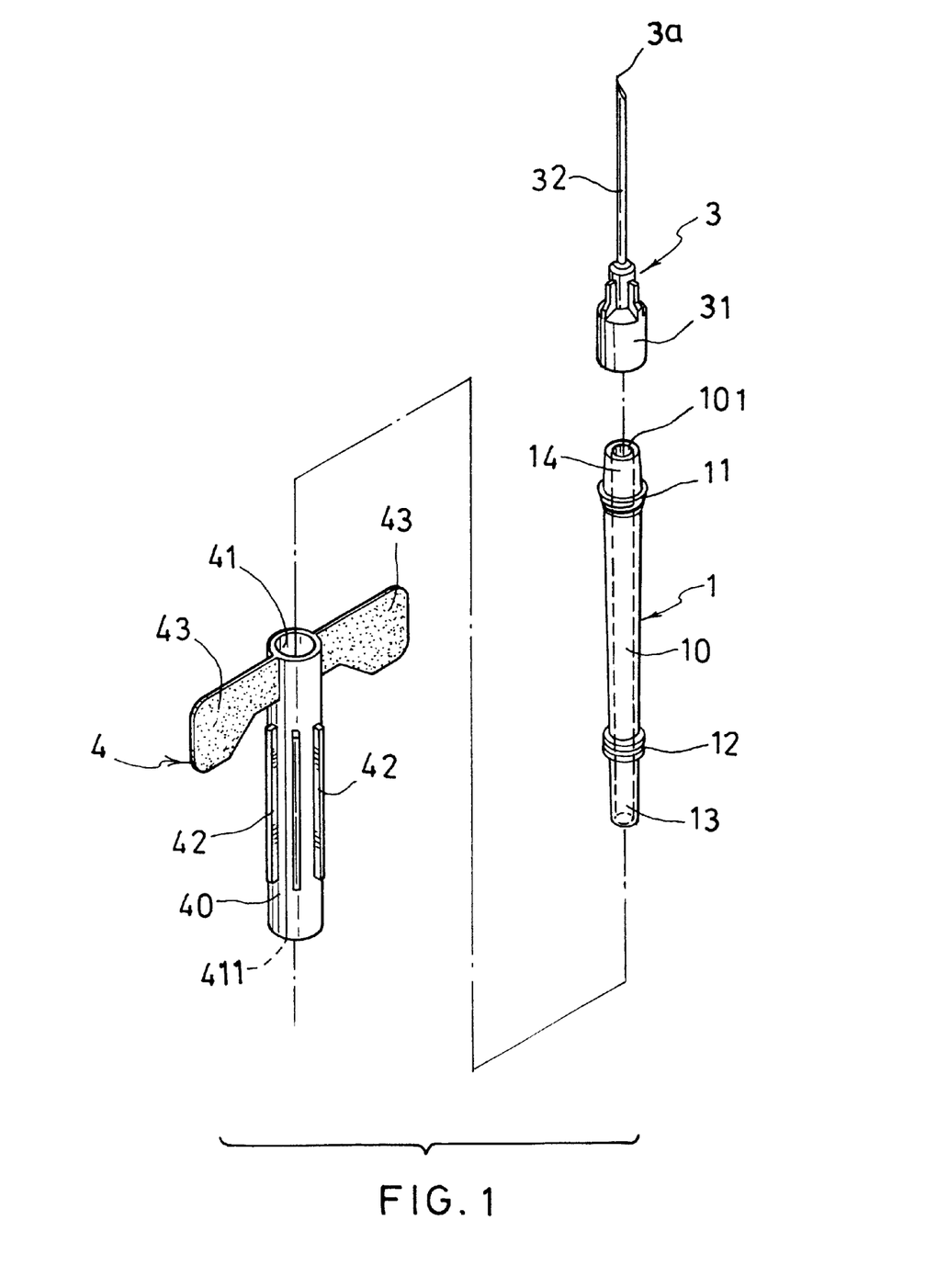
FIG. 1 is a perspective exploded view of the present invention.

The connecting tube 1 includes an axially extending tube body 10 made of hard material. The tube body 10 is formed with a central axial through hole 101 as a path for liquid medicine. The upper engaging section 11 is formed near the top end of the tube body 10 for engaging with the sheath 4. The lower engaging section 12 is formed near the bottom end of the tube body 10 for engaging with the sheath 4. A first coupling section 13 is formed at the bottom end of the tube body 10 for fitting with an infusion hose 2 such as a dropper infusion hose. A second coupling section 14 is formed at the top end of the tube body 10 for fitting with a needle seat 31 of bottom end of the injection needle 3. The sheath 4 includes a sleeve body 40 formed with a central axial fitting hole 41 in which the connecting tube 1 is slidably fitted. At least one connecting section 411 is formed on the wall of the fitting hole 41 for slidably engaging with the upper or lower engaging section 11, 12 of the connecting tube 1. Multiple axial ribs 42 are formed on outer periphery of the sleeve body 40 for facilitating holding and shifting the sheath 4. Two wings 43 radially outward extend from opposite sides of the sleeve body 40 for attaching to the skin of a patient during injection so as to avoid slippage of the injection needle 3.

Figure 2:
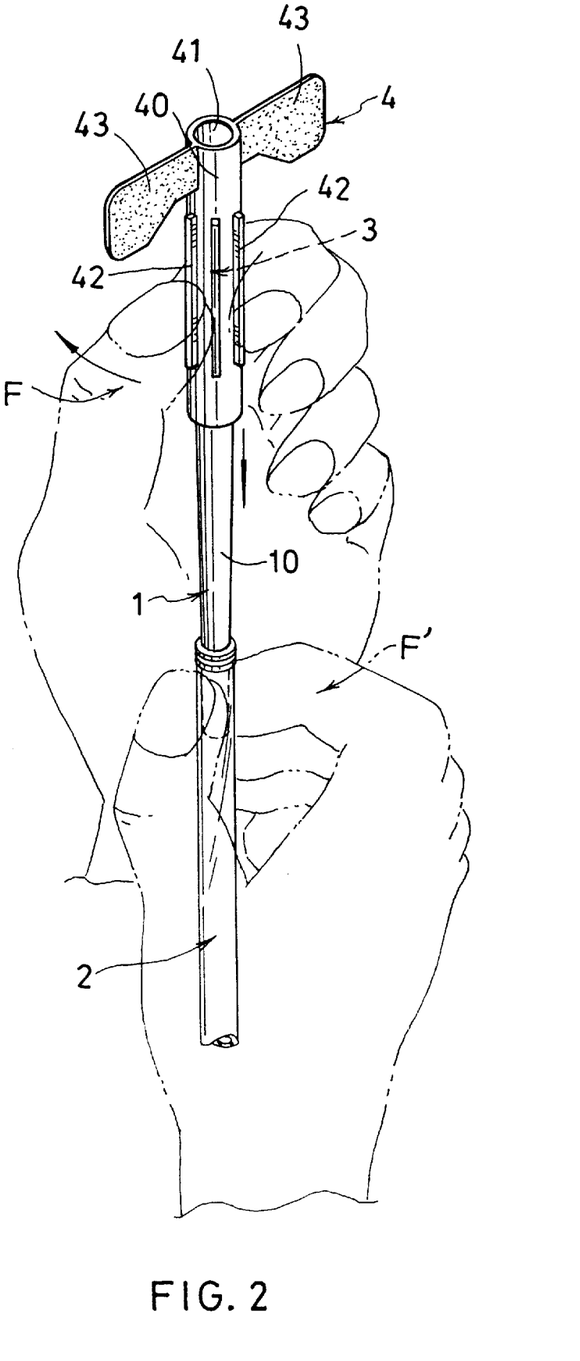
FIG. 2 is a perspective assembled view of the present invention, showing that the sheath is pulled downward.
Figure 3:
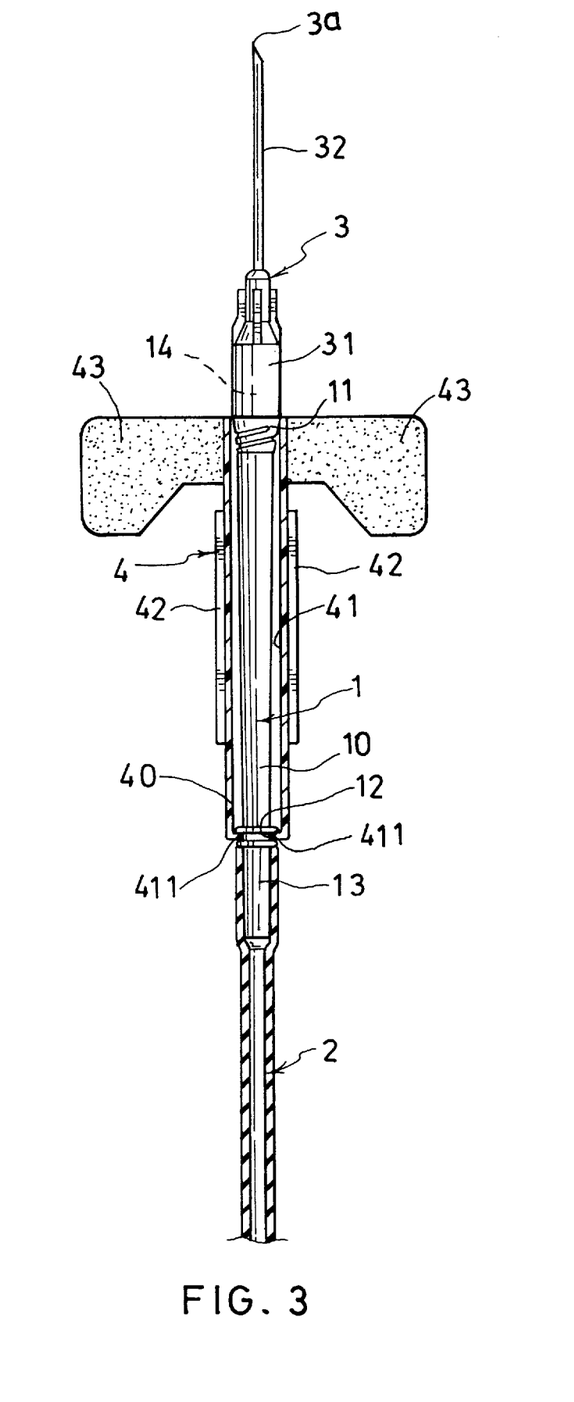
FIG. 3 is a sectional view of the present invention in an injection state.
Figure 4:
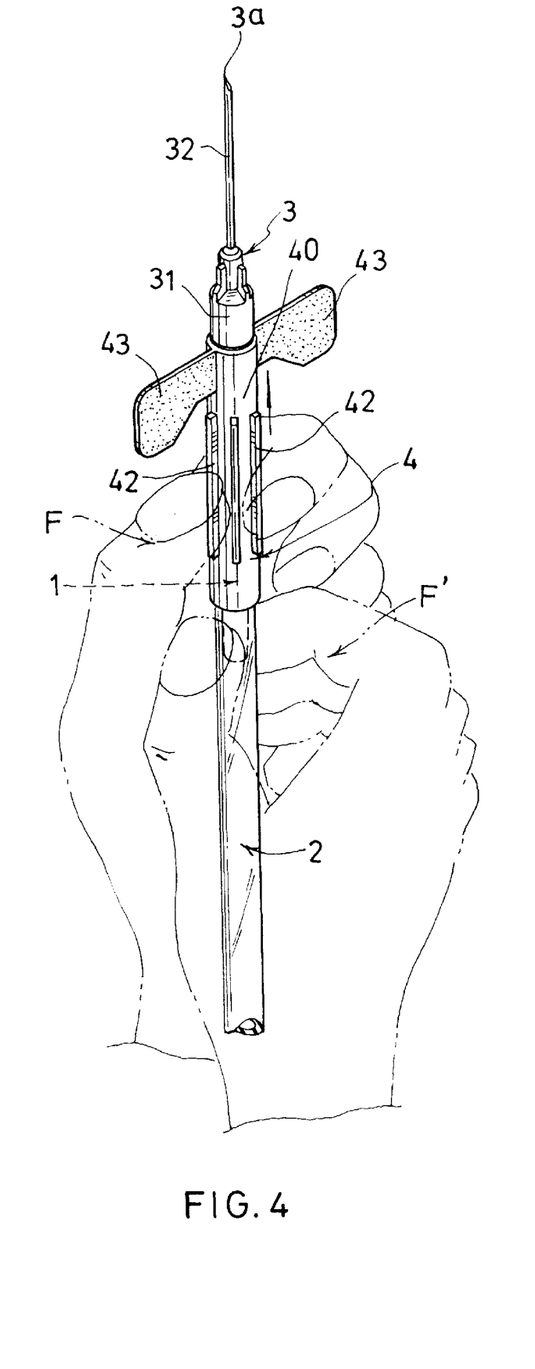
FIG. 4 shows that the sheath is pushed upward from an injection state.
Figure 5:
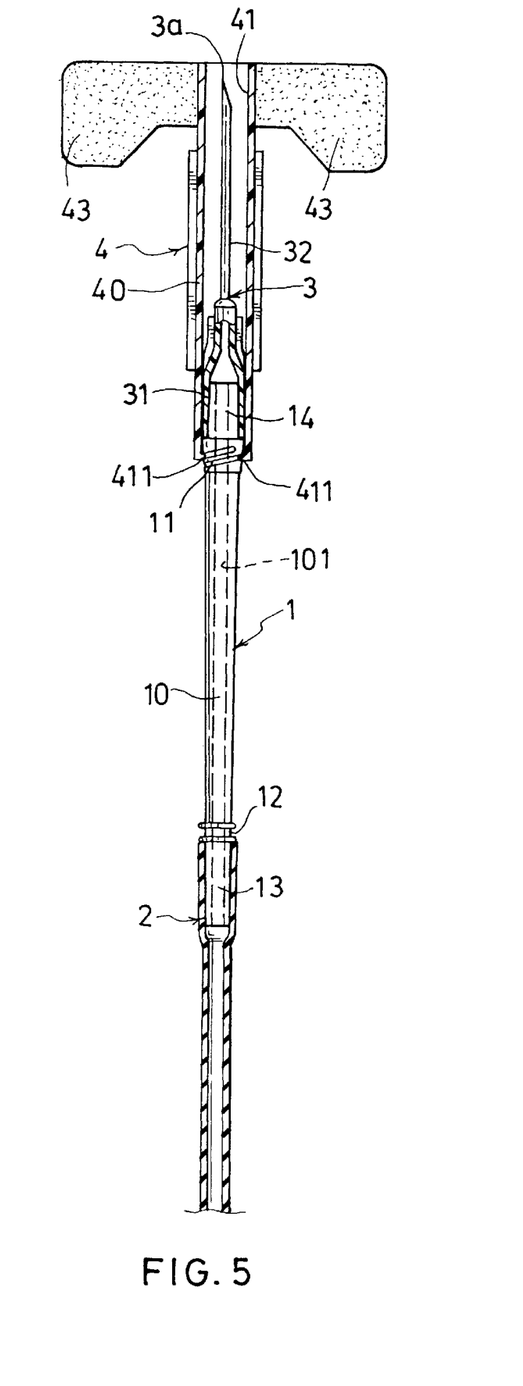
FIG. 5 is a sectional view showing that the injection needle is hidden in the sheath.

The upper engaging section 11 of the connecting tube 1 is formed with an inclined conic head section disposed with a spiral groove, whereby the connecting section 411 of the sheath 4 can be screwed with the spiral groove to secure the sheath 4 on the connecting tube 1 for enclosing the needle 3 in the sheath 4. The lower engaging section 12 of the connecting tube 1 is formed with a latch groove, whereby the sheath 4 can be slided downward to engage the connecting section 411 with the latch groove so as to locate the sheath 4 at the bottom end of the connecting tube 1. Under such circumstance, the needle section 32 of the injection needle 3 extends out of the sheath 4 for injection. The injection needle 3 can be replaced as necessary by other kinds of injection needles such as I.V. fustula set, scalp vein set and dropper injection needle. In use, as shown in FIG. 2, the sleeve body 40 of the sheath 4 and the bottom of the connecting tube 1 are respectively held by two hands F, F' and the sheath 4 is rotated to unlatch the connecting section 411 from the upper engaging section 11. Then the sheath 4 is pulled downward to engage the connecting section 411 with the lower engaging section 12. At this time, the needle section 32 of the injection needle 3 connected at the top end of the connecting tube 1 protrudes outside the sheath 4 for injection as shown in FIG. 3. As shown in FIG. 4, after the injection is completed, the sheath 4 and the bottom of the connecting tube 1 are respectively held by two hands F, F' and the sheath 4 is pushed upward from the bottom of the connecting tube 1 to engage the connecting section 411 with the upper engaging section 11. At this time, the injection needle 3 is totally hidden in the fitting hole 41 of the sheath 4 to avoid impalement of medical personnel.

It should be noted that when downward pulling or upward pushing the sheath 4, the two hands F, F' are both positioned behind the needle tip 3a of the injection needle 3. Therefore, during operation, the accidental impalement can be avoided.

Figure 6:
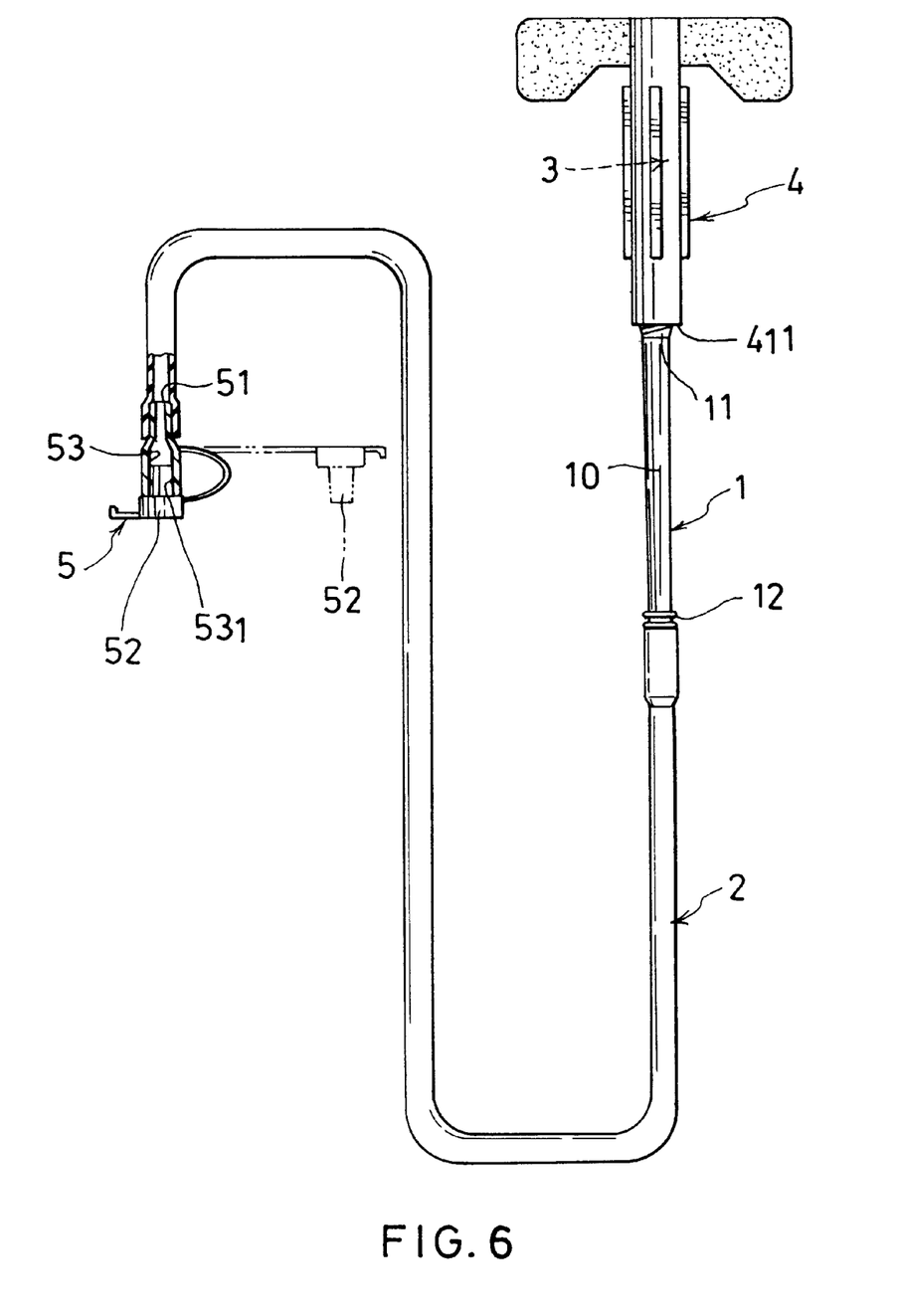
FIG. 6 shows that a hose connector is fitted with an end of the infusion hose connected with the connecting tube of the present invention.
Figure 7:
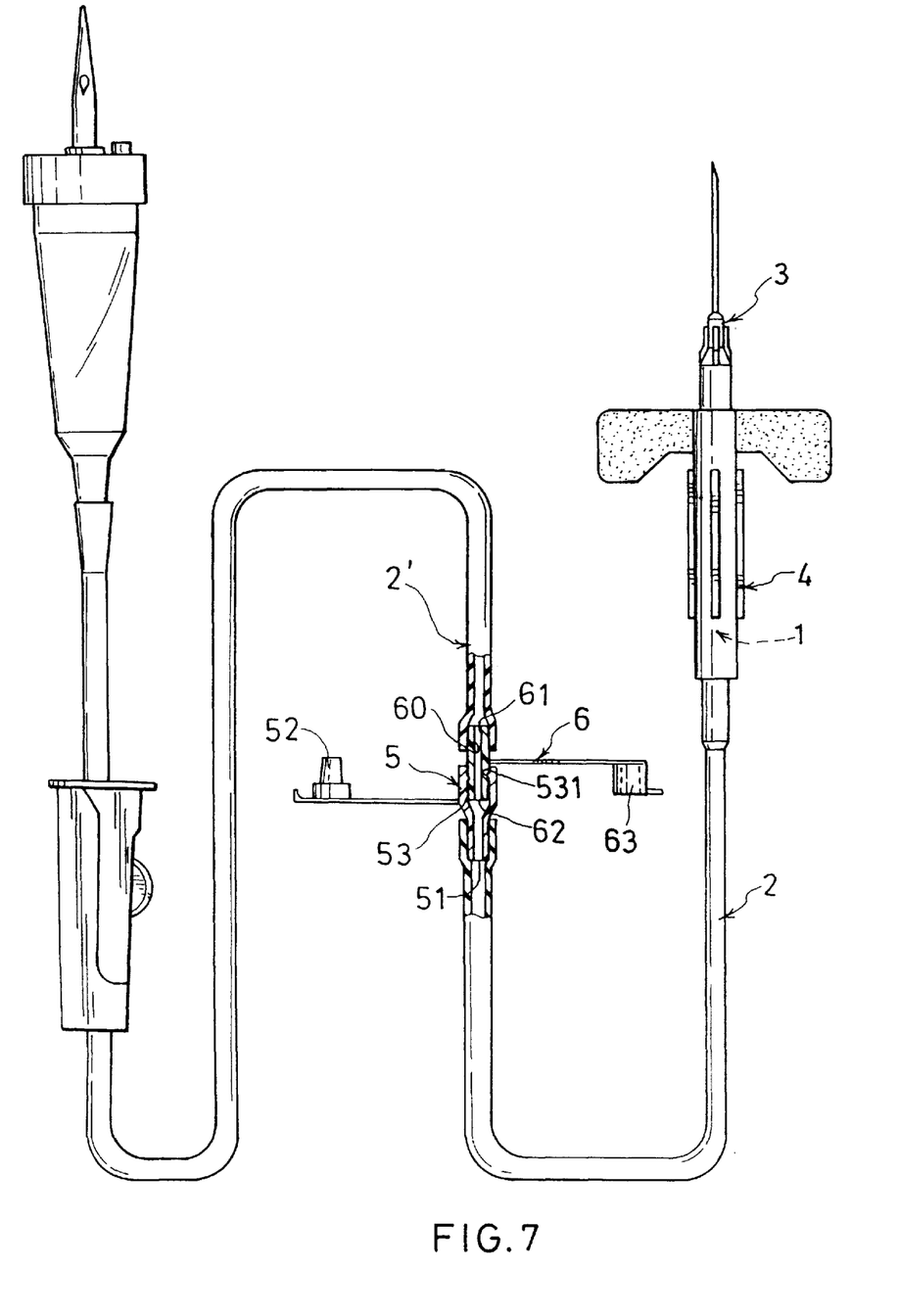
FIG. 7 shows that the present invention is connected with an infusion hose via the hose connector.

Referring to FIG. 6, the end of the infusion hose 2 is fitted with a connecting section 51 of a hose connector 5. A cock 52 is fitted in an end of a through hole 53 of the connector 5. Therefore, the present invention can be applied to I.V. fustula set, scalp vein set and general infusion set. Alternatively, as shown in FIG. 7, the hose connector 5 can be connected with a general infusion hose 2' via a plug 6 to form a general dropper infusion set. Therefore, the present invention can be widely used to reduce the types of used injection needles.

The plug 6 is formed with a central hole 60. A first insertion section 61 extends from the bottom end of the plug 6 for fitting into the infusion hose 2'. A second insertion section 62 is formed at top end of the plug 6 for fitting into the through hole 53 of the hose connector 5. A cap member 63 integrally extends from the plug 6 for fitting with the second insertion section 62 so as to prevent the liquid medicine in the infusion hose 2' from flowing outside. In order to enhance the tightness of connection between the second insertion section 62 and the hose connector 5, at least one leakproof annular rib 531 is formed on the wall of the through hole 53 of the hose connector 5 for tightly fitting with the second insertion section 62. Therefore, the danger that the liquid medicine flows outside or the air get into the infusion hose can be eliminated.

Figure 8:
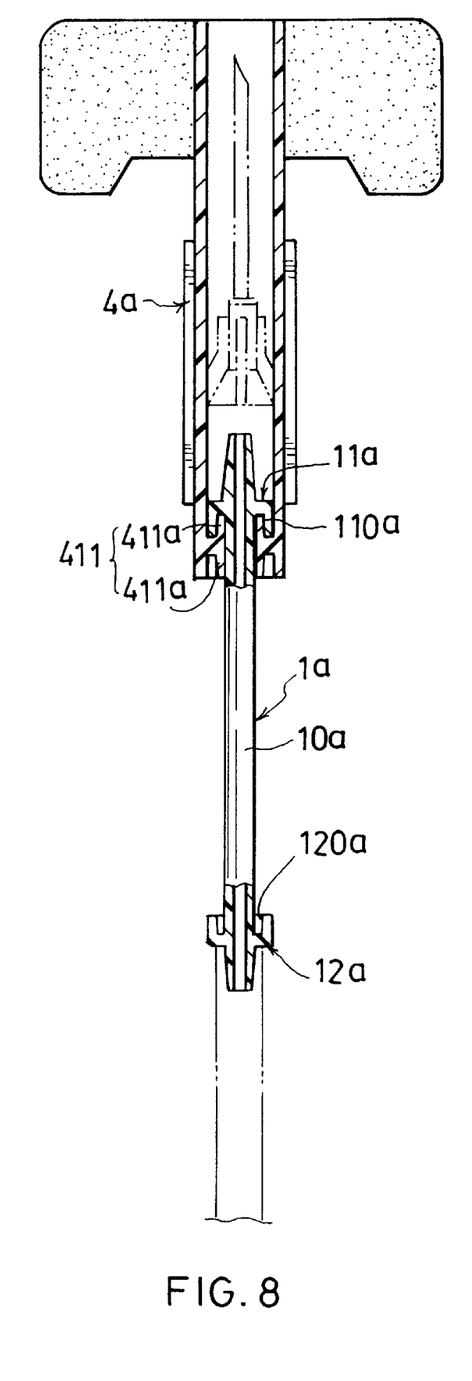
FIG. 8 shows a second embodiment of the connecting tube of the present invention.

FIG. 8 shows another aspect of the connecting tube 1a in which the upper and lower engaging sections 11a and 12a are formed as a pair of opposite annular latch grooves 110a, 120a. In addition, the connecting section 411 of the sheath 4a is formed with a pair of projecting rings 411a respectively extending upward and downward. When the sheath 4a is slided up and down along the tube body 10a of the connnecting tube 1a, the projecting rings 411a can be respectively engaged and tightly located in the annular latch grooves 110a, 120a.

Figures 9, 9A:
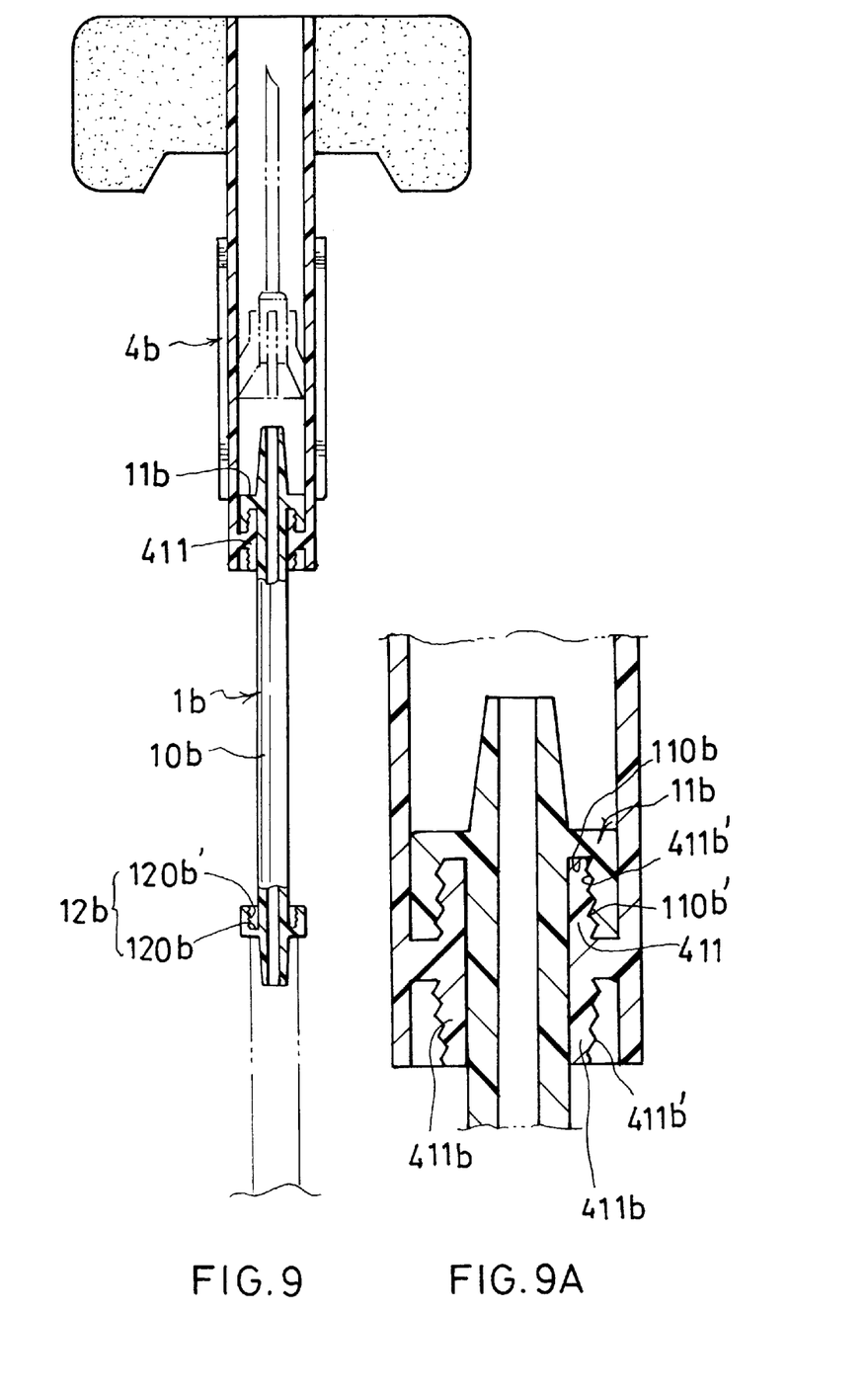
FIG. 9 shows a third embodiment of the connecting tube of the present invention.
FIG. 9A is a partially enlarged view according to FIG. 9.

FIGS. 9 and 9A show still another aspect of the connecting tube 1b in which which the upper and lower engaging sections 11b and 12b are formed as a pair of opposite annular latch grooves 110b, 120b. At least one projecting tooth 110b', 120b' is disposed in each annular latch groove 10b, 120b. In addition, the connecting section 411 of the sheath 4b is formed with a pair of projecting rings 411b. The outer edge of each projecting ring 411b is formed with at least one projecting tooth 411b'. Accordingly, when the sheath 4b is slided up and down along the tube body 10b of the connnecting tube 1b, the projecting rings 411b can be respectively engaged and tightly located in the annular latch grooves 110b, 120b with the projecting tooth 411b' of the projecting ring 411b engaged with the projecting tooth 110b', 120b' of the upper or lower engaging section 11b, 12b.

Figure 10:
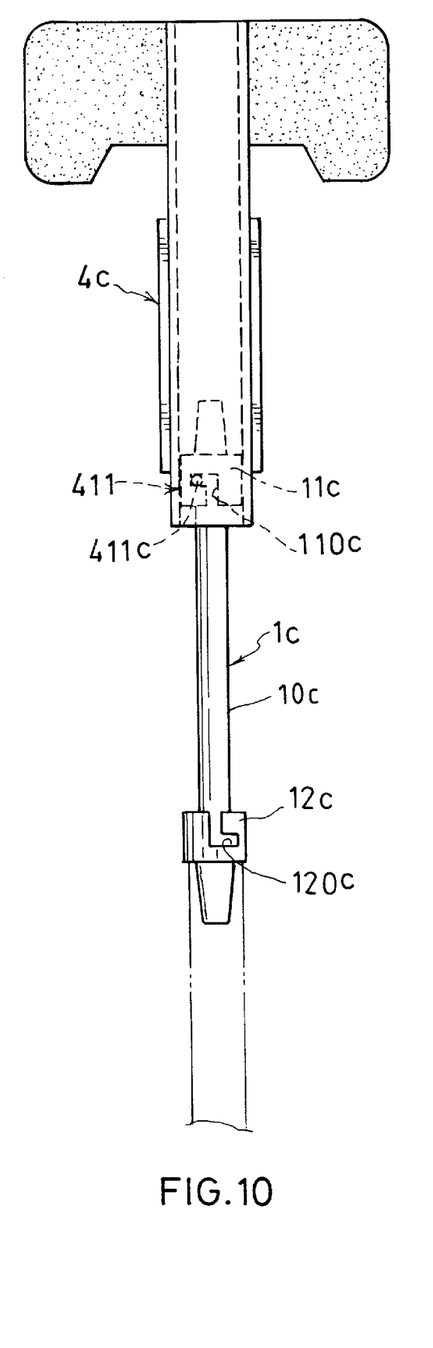
FIG. 10 shows a fourth embodiment of the connecting tube of the present invention.

FIG. 10 shows still another aspect of the connecting tube 1c in which the upper and lower engaging sections 11c and 12c are formed as a pair of opposite L-shaped annular grooves 110c, 120c. In addition, the connecting section 411 of the sheath 4c is formed with at least one projecting pin 411c. When the sheath 4c is slided up and down along the tube body 10c of the connnecting tube 1c, the projecting pin 411c can be rotarily inserted and tightly located in the L-shaped annular grooves 110c, 120c.

Figure 11:
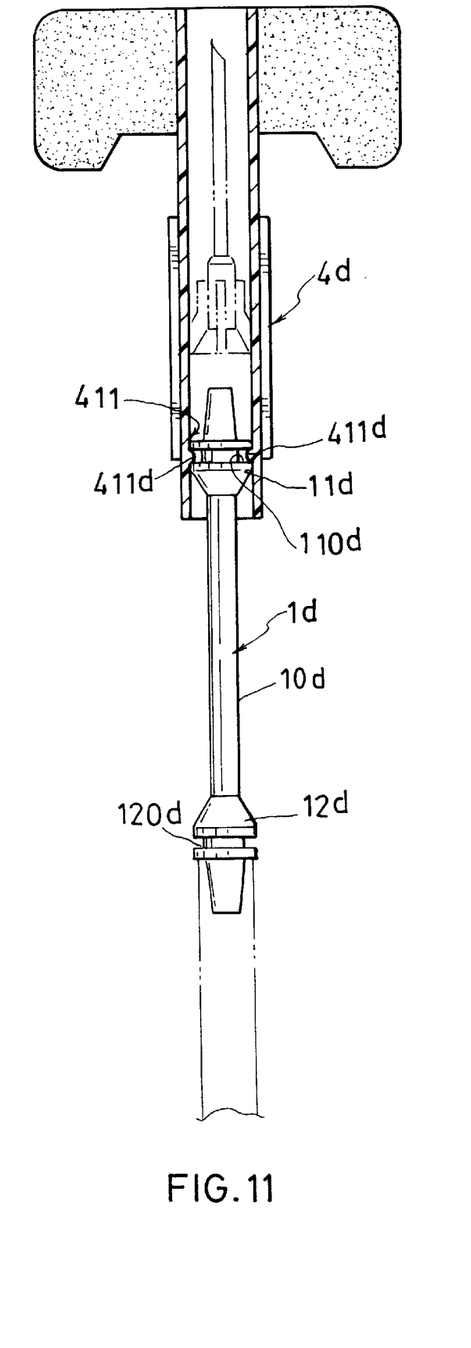
FIG. 11 shows a fifth embodiment of the connecting tube of the present invention.

FIG. 11 shows still another aspect of the connecting tube 1d in which the upper and lower engaging sections 11d and 12d are formed as a pair of opposite annular grooves 10d, 120d. In addition, the connecting section 411 of the sheath 4d is formed with at least one projecting pin 411d. When the sheath 4d is slide up and down along the tube body 10d of the connnecting tube 1d, the projecting pin 411d can be inserted and tightly located in the annular grooves 110d, 120d.

Figure 12:
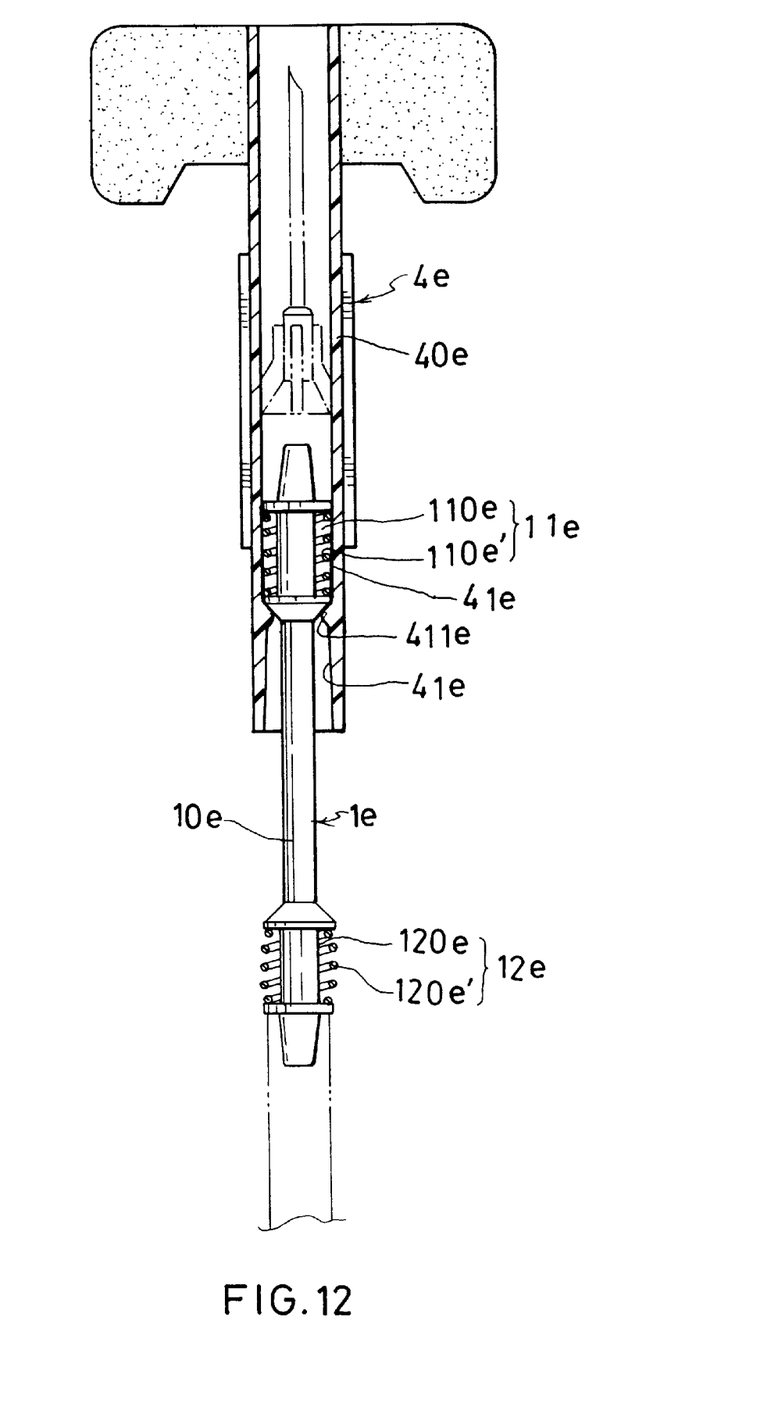
FIG. 12 shows a sixth embodiment of the connecting tube of the present invention.

FIG. 12 shows still another aspect of the connecting tube 1e in which the upper and lower engaging sections 11e and 12e are formed as a pair of opposite spring annular grooves 110e, 120e in which two springs 110e', 120e' are fitted. In addition, the connecting section 411 of the sheath 4e is formed as a stopper flange 411e. The free end of the stopper flange 411e is gradually outward inclinedly expanded. When the sheath 4e is slided up and down along the tube body 10e of the connnecting tube 1e, the springs 110c', 120e' respectively resiliently abut against the walls of the fitting hole 41e on upper and lower sides of the stopper flange 411e to tightly locate the sheath 4e.

The present invention is characterized in that the infusion hose 2 is connected with the bottom end of the hard connecting tube 1. An injection needle 3 is connected with the top end of the connecting tube 1. The connecting tube 1 is disposed with an upper and a lower engaging sections 11, 12, whereby the sheath 4 fitted around the connecting tube 1 can be slid upward therealong to tightly engage with the upper engaging section 11 so as to enclose and hide the injection needle 3 in the sheath 4 without protruding outside.

The advantages of the present invention are as follows:

1. After used, the injection needle 3 is hidden in the sheath 4 without protruding outside. Therefore, the accidental impalement of medical personnel is avoided and the safety is ensured.

2. The single type of infusion set is widely applicable to all of (I.V.) fustula set, scalp vein set and general dropper infusion needles. Therefore, the types of used injection needles are reduced.

3. The infusion set of the present invention has simple structure and can be easily operated.

It should be noted that the above description and accompanying drawings are only used to illustrate some embodiments of the present invention, and are not intended to limit the scope thereof. Any modification of the embodiments should fall within the scope of the present invention.

What is claimed is:

1. A multifunction safety infusion set, comprising:
 a connecting tube including a tube body formed with an axial through hole, an upper engaging section formed at an upper portion of the tube body, and a lower engaging section formed at a lower portion of the tube body, the upper and lower engaging sections of the connecting tube each having an annular flange spaced from an external surface of the tube body to define an annular latch groove therebetween, the annular flanges being oppositely directed;

an injection needle connected to a top end of the tube body;

an infusion hose being connected to a bottom end of the tube body; and, a wing-equipped sheath including a sleeve body formed with a central axial fitting hole through which the tube body of the connecting tube is slidably disposed, at least one connecting section being formed on a wall of the fitting hole for slidable engagement with a selected one of the upper and lower engaging sections of the connecting tube, the connecting section of the sheath being formed with a pair of oppositely directed annular projecting rings extending therefrom in aligned relationship with a respective one of the annular latch grooves, whereby the injection needle is totally retracted and hidden in the fitting hole of the sheath when the connecting section is engaged with the upper engaging section of the connecting tube, and the injection needle protrudes beyond the sheath when the connecting section is engaged with the lower engaging section of the connecting tube.

2. A multifunction safety infusion set, comprising:

a connecting tube including a tube body formed with an axial through hole, an upper engaging section formed at an upper portion of the tube body, and a lower engaging section formed at a lower portion of the tube body, the upper and lower engaging sections of the connecting tube each having an annular flange spaced from an external surface of the tube body to define an annular latch groove therebetween, at least one first projecting tooth being formed on each annular flange to extend into a respective annular latch groove, the annular flanges being oppositely directed;

an injection needle connected to a top end of the tube body;

an infusion hose being connected to a bottom end of the tube body; and, a wing-equipped sheath including a sleeve body formed with a central axial fitting hole through which the tube body of the connecting tube is slidably disposed, at least one connecting section being formed on a wall of the fitting hole for slidable engagement with a selected one of the upper and lower engaging sections of the connecting tube, the connecting section of the sheath being formed with a pair of oppositely directed annular projecting rings extending therefrom in aligned relationship with a respective one of the annular latch grooves, an outer edge of each projecting ring being formed with at least one second projecting tooth extending in a direction opposite a respective first projecting tooth for releasable engagement therewith, whereby the injection needle is totally retracted and hidden in the fitting hole of the sheath when the connecting section is engaged with the upper engaging section of the connecting tube, and the injection needle protrudes beyond the sheath when the connecting section is engaged with the lower engaging section of the connecting tube.

3. A multifunction safety infusion set, comprising:

a connecting tube including a tube body formed with an axial through hole, an upper engaging section formed at an upper portion of the tube body, and a lower engaging section formed at a lower portion of the tube body, the upper and lower engaging sections of the connecting tube each having an annular groove formed therein and a spring disposed in the groove, the tube body extending through the springs;

an injection needle connected to a top end of the tube body;

an infusion hose being connected to a bottom end of the tube body; and, a wing-equipped sheath including a sleeve body formed with a central axial fitting hole through which the tube body of the connecting tube is slidably disposed, at least one connecting section being formed on a wall of the fitting hole for slidable engagement with a selected one of the upper and lower engaging sections of the connecting tube, the connecting section of the sheath being formed with a flange extending into the fitting hole and having inclined surfaces, whereby the injection needle is totally retracted and hidden in the fitting hole of the sheath when the connecting section is engaged with the upper engaging section of the connecting tube, and the injection needle protrudes beyond the sheath when the connecting section is engaged with the lower engaging section of the connecting tube, an outer surface of the springs respectively abut against an inner surface of the fitting hole on a respective portion above and below the flange to tightly locate the sheath.

* * * * *